(12) United States Patent
Bang et al.

(10) Patent No.: US 11,852,475 B2
(45) Date of Patent: Dec. 26, 2023

(54) OPTICAL COHERENCE TOMOGRAPHY SYSTEM

(71) Applicant: Danmarks Tekniske Universitet, Kgs. Lyngby (DK)

(72) Inventors: Ole Bang, Kgs. Lyngby (DK); Deepak Jain, Kgs. Lyngby (DK); Christian Rosenberg Petersen, Kgs. Lyngby (DK); Niels Møller Israelsen, Kgs. Lyngby (DK); Christos Markos, Kgs. Lyngby (DK)

(73) Assignee: Danmarks Tekniske Universitet, Kgs. Lyngby (DK)

(*) Notice: Subject to any disclaimer, the term of this patent is extended or adjusted under 35 U.S.C. 154(b) by 0 days.

(21) Appl. No.: 17/283,224

(22) PCT Filed: Oct. 8, 2019

(86) PCT No.: PCT/EP2019/077239
§ 371 (c)(1),
(2) Date: Apr. 6, 2021

(87) PCT Pub. No.: WO2020/074524
PCT Pub. Date: Apr. 16, 2020

(65) Prior Publication Data
US 2021/0389115 A1 Dec. 16, 2021

(30) Foreign Application Priority Data
Oct. 8, 2018 (EP) .................................. 18199201

(51) Int. Cl.
*G01B 9/02* (2022.01)
*G01B 9/02091* (2022.01)
(Continued)

(52) U.S. Cl.
CPC ..... *G01B 9/02044* (2013.01); *G01B 9/02091* (2013.01); *A61B 3/102* (2013.01); *A61B 5/0066* (2013.01)

(58) Field of Classification Search
CPC ........... G01B 9/02044; G01B 9/02091; A61B 3/102; A61B 5/0066; G01J 3/108; G02F 1/35; G02F 1/365
See application file for complete search history.

(56) References Cited

U.S. PATENT DOCUMENTS 7,519,253 B2  4/2009  Islam
2005/0036150 A1*  2/2005  Izatt ................... G01B 9/02044
                                                              356/479

(Continued)

FOREIGN PATENT DOCUMENTS

WO  2015003721 A1  1/2015
WO  2018007572 A1  1/2018

OTHER PUBLICATIONS

Mason, Elliott J.. "Applications of optical parametric downconversion: I. Self-phase locking, II. Generation of entangled photon pairs in periodically-poled lithium niobate." (2002). (Year: 2002).*

(Continued)

*Primary Examiner* — Uzma Alam
*Assistant Examiner* — Jonathan Cook
(74) *Attorney, Agent, or Firm* — Knobbe, Martens, Olson & Bear, LLP (57) ABSTRACT

Disclosed is an OCT system, in particular a mid-IR OCT system, comprising:
an upconversion module configured to frequency upconvert light received or receivable by the upconversion module and which is in a wavelength range between a first wavelength and a higher second wavelength, the difference between the second wavelength and the first wavelength being at least 300 nm or larger, and (Continued)

the wavelength range having a center wavelength at 2.8 µm or larger, the center wavelength being defined by the average value between the first wavelength and the second wavelength.

18 Claims, 6 Drawing Sheets

(51) Int. Cl.
  *A61B 3/10* (2006.01)
  *A61B 5/00* (2006.01)

(56) References Cited

U.S. PATENT DOCUMENTS

| | | | | |
|---|---|---|---|---|
| 2010/0271635 | A1* | 10/2010 | Resch | G01B 9/02004 356/477 |
| 2015/0192732 | A1 | 7/2015 | Moselund et al. | |
| 2017/0356734 | A1 | 12/2017 | Hendon et al. | |
| 2020/0183250 | A1* | 6/2020 | Hall | G02F 1/365 |

OTHER PUBLICATIONS

Thorlabs, "Periodically Poled Lithium Niobate (PPLN)—Tutorial" Captured on the wayback machine: https://web.archive.org/web/20140124082111/https://www.thorlabs.com/catalogpages/693.pdf (Year: 2014).*

P. G. Schunemann, L. A. Pomeranz, D. J. Magarrell, J. C. McCarthy, K. T. Zawilski and D. E. Zelmon, "1064-nm-Pumped mid-infrared optical parametric oscillator based on orientation-patterned gallium phosphide (OP-GaP)," 2015 Conference on Lasers and Electro-Optics (CLEO), 2015, pp. 1-2. (Year: 2015).*

Chosrowjan, H., Taniguchi, S. and Tanaka, F. (2015), Ultrafast fluorescence upconversion technique and its applications to proteins. FEBS J, 282: 3003-3015. https://doi.org/10.1111/febs.13180 (Year: 2015).*

Mathez, M. D., Pedersen, C., Rodrigo, P. J., & Tidemand-Lichtenberg, P. Investigation of mid-IR picosecond image upconversion. In Proceedings of SPIE (vol. 10088). [100880L] SPIE—International Society for Optical Engineering. (Proceedings of S P I E—International Society for Optical Engineering) (Year: 2017).*

Romain Demur, Renaud Garioud, Arnaud Grisard, Eric Lallier, Luc Leviandier, Loïc Morvan, Nicolas Treps, and Claude Fabre, "Near-infrared to visible upconversion imaging using a broadband pump laser," Opt. Express 26, 13252-13263 (2018) (Year: 2018).*

Richard Scheps, Upconversion laser processes, Progress in Quantum Electronics, vol. 20, Issue 4, 1996, pp. 271-358, ISSN 0079-6727, https://doi.org/10.1016/0079-6727(95)00007-0. (Year: 1996).*

Up-Conversion Imaging Processing With Field-of-View and Edge Enhancement, Shi-Kai Liu, Chen Yang, Shi-Long Liu, Zhi-Yuan Zhou, Yan Li, Yin-Hai Li, Zhao-Huai Xu, Guang-Can Guo, and Bao-Sen Shi, Phys. Rev. Applied 11, 044013—Published Apr. 4, 2019 (Year: 2019).*

Del Mar Photonics TI:sapphire lasers datasheet, dated Sep. 1, 2013 (https://web.archive.org/web/20130901022604/http://www.dmphotonics.com/Linewidth/Linewidth%20of%20TiSapphire%20CW%20laser.htm) (Year: 2013).*

International Search Report and Written Opinion for International Patent Application No. PCT/EP2019/077239, dated Dec. 20, 2019 in 15 pages.

Moselund et al., "Supercontinuum—broad as a lamp bright as a laser, now in the mid-infrared"; Laser Technology for Defense and Security VIII, SPIE, vol. 8381 No. 1, May 11, 2012.

Paterova et al., "Tunable optical coherence tomography in the infrared range using visible photons"; Quantum Science and Technology, vol. 3 No. 2, Apr. 3, 2018.

Su et al., "Perspectives of mid-infrared optical coherence tomography for inspection and micrometrology of industrial ceramics"; Optics Express, vol. 22, No. 13, Jun. 30, 2014.

\* cited by examiner

```
┌─────────────────────────────────────────┐
│ Project a broadband probe light beam    │
│ onto an analyzed object and a           │   221
│ reference element                       │
└─────────────────────────────────────────┘
                    │
                    ▼
┌─────────────────────────────────────────┐
│ Generate an interference light beam     │
│ from probe light returning from the     │   222
│ analyzed object and reference element   │
└─────────────────────────────────────────┘
                    │
                    ▼
┌─────────────────────────────────────────┐
│ Generate upconverted light beam from    │   223
│ the interference light beam             │
└─────────────────────────────────────────┘
                    │
                    ▼
┌─────────────────────────────────────────┐
│ Record spectrum of the upconverted      │
│ light beam using a spectrometer         │   224
│ covering the near-infrared and/         │
│ or visible wavelenght range             │
└─────────────────────────────────────────┘
                    │
                    ▼
┌─────────────────────────────────────────┐
│ Convert the recorded spectra to A, B    │   225
│ or C scans of the analyzed object       │
└─────────────────────────────────────────┘
```

OPTICAL COHERENCE TOMOGRAPHY SYSTEM

CROSS-REFERENCE TO RELATED APPLICATIONS

This application is the U.S. National Phase under 35 U.S.C. § 371 of International Application PCT/EP2019/077239, filed Oct. 8, 2019, which claims priority to European Patent Application No. 18199201.7, filed Oct. 8, 2018. The disclosures of the above-described applications are hereby incorporated by reference in their entirety.

TECHNICAL FIELD

This disclosure generally relates to Optical Coherence Tomography (OCT) systems.

BACKGROUND

Optical Coherence Tomography (OCT) has been established as one of the most successful and significant optical techniques for biophotonics and clinical biomedical imaging, most notably within the field of ophthalmology and dermatology. OCT has the ability to perform real-time, non-invasive, and non-contact measurements in reflection, providing 3D sample visualization. Rapid advances in light sources, detectors, and components for the visible and near-infrared spectral region has enabled the development of OCT based high-speed and high-resolution in-vivo imaging. The main limitation of OCT is the strong scattering of light at visible and near-IR wavelengths, which limits the penetration depth in turbid media to a few tens to hundreds of microns depending on the analyzed object. Current state-of-the-art commercially available OCT systems for dermatology and non-destructive testing operate in the 1.3 μm wavelength range, utilizing the low water absorption, and the maturity of optical fibers and components developed for telecommunication in this region. At longer wavelengths, light sources and detectors are significantly less efficient and components are less matured.

It is an object of the present invention to provide an improved OCT system which can operate fast, with high resolution, high sensitivity, and provides reduced scattering and thereby increased sample penetration.

SUMMARY

The object is satisfied by an OCT system in accordance with the features of claim 1. Preferred embodiments of the present invention are disclosed in the dependent claims.

An OCT system, in particular a mid-infrared (mid-IR) OCT system, is disclosed. The OCT system comprises:
an upconversion module configured to frequency upconvert light received or receivable by the upconversion module and which is in a wavelength range between a first wavelength and a higher second wavelength, the difference between the second wavelength and the first wavelength being at least 300 nm or larger, and the wavelength range having a center wavelength at 2.8 μm or larger, the center wavelength being defined as the average value of the first wavelength and the second wavelength.

The average value corresponds to half of the sum of the first wavelength and the second wavelength. The light received or receivable by the upconversion module may comprise probe light obtained from exposure of a sample. Thus, the light provided to the upconversion module may be called probe light. The light provided to the upconversion module may also be called interference light. Such light may be generated by interference between probe light and reference light, the latter received from a reference path.

The upconversion module may be used to frequency upconvert a light spectrum in the above mentioned, predefined mid-IR wavelength range to an upconverted light spectrum having higher frequencies and, correspondingly, shorter wavelengths than the original mid-IR light spectrum. The upconversion module therefore allows to carry out a measurement on a sample using a light spectrum in the mid-IR or even in the far-IR frequency range. The light spectrum received from the sample may contain information about the sample and this light spectrum can be upconverted by the upconversion module to an upconverted light spectrum which is, e.g., in the near-IR region. In this region, fast, low-noise, highly sensitive and low-cost sensor elements can be used for the detection and analysis of the often weak sample light signals back-scattered from sub-surface structures of the scanned sample. The mid-IR OCT system therefore allows for carrying out sensitive measurements on samples using mid-IR wavelengths and for detecting the received signals in a low noise and highly sensitive fashion at near-IR wavelengths, in particular due to the presence of the upconversion module.

The system may comprise a light source, in particular a mid-IR broadband light source, configured for providing a probe light beam which has a spectrum that at least comprises a continuous spectral region between the first wavelength and the second wavelength.

Preferably, the wavelength range between the first wavelength and the second wavelength that can be frequency upconverted is a continuous wavelength range. All spectral components in the wavelength range can therefore be frequency upconverted by the upconversion module.

Preferably, the upconversion module is configured to employ a pump light beam having a wavelength which is smaller than the first wavelength for frequency upconversion of the light in the wavelength range between the first and second wavelengths.

Preferably, the wavelength of the upconversion pump light beam, XP, is in the range of 600 nm to 1.8 μm, such as in the range of 800 nm to 1.5 μm.

The upconversion module may operate by sum frequency generation using the pump light beam of the upconversion module and the light coming from the sample in the wavelength range between the first and second wavelength. The upconversion module may not employ second harmonic generation (SHG) for upconverting the light.

The difference between the first wavelength and the second wavelength may preferably be smaller than 15 μm or 10 μm or 5 μm or 2 μm or 1 μm.

Preferably, the system further comprises an interferometer configured for receiving a probe light beam from a light source and for dividing the received probe light beam into a sample path and a reference path and for generating an interference light beam by combining probe light returning from the sample path with probe light returning from the reference path, and the upconversion module may be configured to receive the interference light beam for generating an upconverted light beam by frequency upconversion of the interference light beam.

The system may also comprise a detector configured to receive the frequency upconverted light from the upconversion module and for detecting spectral properties of the upconverted light.

The upconversion module may comprise an upconversion element configured to enable parametric wavelength conversion, the upconversion element may comprise a quadratic nonlinear material, and the pump source may be arranged for launching a pump light beam into the upconversion element.

The pump light beam provided by the pump source to the upconversion element can be pulsed. The probe light beam may be pulsed and the pulses of a pump light beam used in the upconversion module are synchronized and overlapping with the pulses of the probe light beam.

The pump light beam provided by the pump source to the upconversion element can be a continuous wave (cw) laser beam. The laser beam can have a spectral width which is lower than 10 nm, or 5 nm, or 1 nm, or 0.75 nm, or 0.5 nm, or 0.4 nm, or 0.3 nm, or 0.2 nm, or 0.1 nm. The use of a cw laser pump beam helps to obtain a high resolution OCT system and to increase the imaging depth after upconversion.

The upconversion module may operate by non-collinear interaction between the interference light beam and a pump light beam of the upconversion module. Also a collinear interaction between the interference light beam and a pump light beam of the upconversion module may be possible. There may also be a spatially varying poling period.

The probe light beam can be focused within an upconversion element of the upconversion module. The pump light beam can be focused within the upconversion element. The probe light beam cannot be focused within the upconversion element. The pump light beam cannot be focused within the upconversion element. The probe light beam can be unfocused or non-focused within the upconversion element. The pump light beam can be unfocused or non-focused within the upconversion element. If the probe light beam and/or the pump light beam is not focused or unfocused or non-focused in the upconversion element, the respective beam might travel through the upconversion element in form of a collimated beam.

The detector may be configured to detect light within a range of wavelengths extending from 390 nm to 2 µm, such as in the range of 390 nm to 900 nm or in the range of 900 nm to 1600 nm.

The detector may comprise a spectrometer, such as a silicon-based, Ge-based or InGaAs-based spectrometer. Alternatively or additionally, the detector may include a thermopile and/or a pyrodetector adapted to detect light, in particular in the above mentioned wavelength range.

The system may comprise a long-pass filter arranged to block wavelengths in the light received from a broadband light source of the system below a defined cut-on wavelength. The broadband light source may be a supercontinuum (SC) light source and/or may include a light spectrum that extends at least between the first wavelength and second wavelength.

A method for analyzing an object using an OCT system is also disclosed. The method comprises:
  providing a probe light beam,
  dividing the probe light beam into a sample path and a reference path, where probe light in the sample path is projected onto the object;
  generating an interference light beam by combining probe light returning from the sample path with probe light returning from the reference path;
  generating an upconverted light beam by frequency upconversion of the spectral components in the interference light beam which are in a wavelength range between a first wavelength and a higher second wavelength, the difference between the second wavelength and the first wavelength being at least 300 nm or larger, and the wavelength range having a center wavelength at 2.8 µm or larger, the center wavelength being defined by the average value between the first wavelength and the second wavelength, and
  detecting the spectral properties of the upconverted light beam.

Disclosed is also an OCT system comprising:
  a mid-IR broadband light source configured for providing a probe light beam;
  an interferometer configured for receiving the probe light beam and for dividing the received probe light beam into a sample path and a reference path and for generating an interference light beam by combining probe light returning from the sample path with probe light returning from the reference path;
  an upconversion module configured for generating an upconverted light beam by frequency upconversion of the interference light beam; and
  a detector configured for detecting the spectral properties of the upconverted light beam.

Disclosed is also a method for analyzing an object using an OCT system, the method comprising:
  providing a mid-infrared broadband probe light beam;
  dividing the probe light beam into a sample path and a reference path, where probe light in the sample path is projected onto the analyzed object and where probe light in the reference path is reflected by a reflector;
  generating an interference light beam by combining probe light returning from the sample path and with probe light returning from the reference path;
  generating an upconverted light beam by frequency upconversion of the interference light beam; and
  detecting the spectral properties of the upconverted light beam.

In the interferometer an optical element, such as a beam splitter or a fiber coupler, may divide the probe light beam into sample and reference paths. The probe light propagating along the sample path may be projected onto the analyzed object where it is backscattered from either the surface or sub-surface structures in the object. Meanwhile, the portion of the probe light divided into the reference path may be reflected by a reflective element, such as a mirror arranged in the reference path. The reflected beams may be combined in the interferometer to generate an interference light beam with light in substantially the same wavelength range as the reflected beams. The interference light beam may contain information from which the sub-surface structure of the object and its reflective properties can be derived.

A so-called A-scan may express refractive index variations in the analyzed object below a given point on the object surface and the A-scan may be determined by analyzing interferograms obtained at that particular point. Repeating the analysis at different points along a line or over a grid on the object surface can provide so-called B-scans or C-scans with 2D data or 3D data, respectively, of the refractive index variations in the material of the analyzed objects.

The upconversion module may be configured for generating an upconverted light beam from the received interference light beam, where the upconverted light beam has shorter wavelengths/higher frequencies than the interference light beam. In particular, the center wavelength of the upconverted light beam is smaller than the center wavelength of the probe light beam. The shorter wavelengths of the upconverted light beam may provide that even when using the mid-IR probe light to provide a good penetration depth into the object, the upconverted light can still be analyzed using detectors operating, e.g., in the visible or near-infrared wavelengths ranges. Mid-IR detectors are expensive and relatively slow due to a low responsivity and sensitivity. In contrast, low-cost, highly-sensitive, and fast detectors are commercially available for wavelengths in the range from 390 nm to 2 μm. Thus generating an upconverted light beam from the interference light beam with shorter wavelengths relative to the mid-IR interference light beam allows for a faster detection and ultimately real-time scanning while still obtaining the advantage of employing mid-IR probe light in the measurement to provide deeper penetration into the analyzed sample.

In the context of the current disclosure, the phrase "mid-infrared broadband light source" refers to a light source configured to emit light in a continuum of wavelengths where at least a part of the emitted continuum is within the range extending from 2.6 μm to 20 μm, preferably to 25 μm.

The wavelength ranges from about 390 nm to about 700 nm and from about 700 nm to about 2 μm are often referred to as the visible and the near-infrared wavelength ranges, and the detector technology is more mature for these wavelength ranges compared to the mid-IR range.

First/Center Wavelength vs Penetration Depth

In some embodiments, the center wavelength of the probe light beam is larger than 2.8 μm, such as larger than 3 μm, such as larger than 3.5 μm, such as larger than 4 μm, such as larger than 5 μm, such as larger than 6 μm, such as larger than 7 μm, such as larger than 10 μm. In some embodiments, the center wavelength of the probe light is in the range of 2.8 μm to 15 μm, such as in the range of 3 μm to 10 μm.

The penetration depth of the probe light into the analyzed object is limited by scattering losses. In OCT systems operating at wavelengths in the visible and near-IR range, scattering limits the penetration depth to a few tens to hundreds of microns in highly scattering turbid materials. Since the scattering losses depend inversely on the probe light wavelength relative to the size of the scattering features, employing probe light with a center wavelength above 2.8 μm can increase the penetration depth of the probe light and may thus allow the OCT system to analyze parts of the sample deeper below the surface compared to e.g. 1300 nm central wavelength OCT systems.

Bandwidth

The broadband probe light beam comprises a continuum of light extending at least over a wavelength range between the first wavelength, $\lambda_1$, and the second wavelength, $\lambda_2$, with the difference between the second wavelength and the first wavelength being at least 300 nm or larger, and the wavelength range having a center wavelength at 2.8 μm or larger, the center wavelength being defined by the average value between the first wavelength and the second wavelength.

The upconversion module is configured to convert light in this defined wavelength range to a second wavelength range extending from a third wavelength, $\lambda_3$, to a fourth wavelength, $\lambda_4$. The second wavelength range is at higher frequencies/lower wavelengths than the original spectral range.

In some embodiments, the bandwidth of the probe light beam is more than 300 nm, such as more than 600 nm, such as more than 800 nm, such as more than 1000 nm, such as more than 1200 nm, such as more than 1500 nm, such as more than 2000 nm.

In some embodiments, the bandwidth of the probe light beam is in the range of 300 nm to 10 μm, such as in the range of 600 nm to 5 μm, such as in the range of 750 nm to 3 μm, such as in the range of 1 μm to 2 μm.

In some embodiments, the first wavelength X$\lambda_1$ is larger than 2.6 μm, such as larger than 2.8 μm, such as larger than 3 μm, such as larger than 3.5 μm, such as larger than 4 μm, such as larger than 5 μm, such as larger than 6 μm, such as larger than 7 μm, such as larger than 10 μm.

Bandwidth vs Axial Resolution

The axial resolution, $\Delta z$, of the OCT measurements depends on the center wavelength, $\lambda_0$, and the bandwidth, $\Delta\lambda$, of the probe light through the ratio $\lambda_0^2/\Delta\lambda$. I.e. the axial resolution of the OCT measurement is proportional to the center wavelength squared and inversely proportional to the bandwidth of the probe light. Increasing the center wavelength of the probe light to obtain data from deeper below the object surface thus results in a poorer axial resolution. However this is compensated at least to some degree by using a large bandwidth light source, for example a supercontinuum light source, such that a good axial resolution and a good penetration depth is obtained simultaneously, i.e., high resolution data can be obtained while analyzing relatively deep below the surface.

Upconversion by Sum Frequency Generation

In some embodiments, the upconversion module at least partly operates by sum frequency generation. I.e. the upconversion module is configured for generating the upconverted light beam at least partly by a sum frequency generation process on the photons of the interference light beam. This may be realized in a nonlinear element, such as a nonlinear crystal, where photons of the interference light beam interact with photons of a pump light beam to generate the photons of the upconverted light beam.

Accordingly, in some embodiments, the upconversion module comprises:
- an upconversion element configured to enable parametric wavelength conversion, where the upconversion element comprises a quadratic nonlinear material; and
- a pump source arranged for launching a pump light beam into the upconversion element.

The upconversion element may be arranged in the path of the interference light beam received from the interferometer and the upconverted light beam may be generated by mixing the photons of the interference light beam with photons from the pump light beam.

The sum-frequency generation process is a parametric process bound by energy and momentum conservation, such that for a photon in the interference light beam having a wavelength of $\lambda_{IR}$ and a propagation vector $\vec{k}_{IR}$, which interacts with a photon from the pump light beam having a wavelength of $\lambda_P$ and a propagation vector $\vec{k}_P$ the generated upconverted photon has a wavelength of $\lambda_{UP}$ and a propagation vector $\vec{k}_{UP}$ according to:

$$\lambda_P^{-1}+\lambda_{IR}^{-1}=\lambda_{UP}^{-1}, \Delta\vec{k}=\vec{k}_{UP}-\vec{k}_P-\vec{k}_{IR}$$

where $\vec{k}$ are the wave propagation vectors, and $\Delta\vec{k}$ is a measure of the phase-mismatch amongst the three interacting light beams, which should ideally be zero for maximum conversion efficiency. I.e. when the nonlinear element is pumped by the pump beam, an upconverted light beam is generated from the interference light beam with the wavelengths of the upconverted light beam depending on the wavelengths of the pump light beam and interference light beam according to the above equation.

The nonlinear upconversion of the mid-IR interference beam is ultra-fast and real-time and when combined with ultra-fast and efficient detection of the upconverted beam by standard commercial near-IR detectors, recording of the interferometric information can be made in real-time.

The sum-frequency generation is preferably realized by pumping the nonlinear element with a narrow-band pump light source, such as a single-frequency laser, to obtain a well-defined frequency upconversion of each wavelength component of the interference light beam thereby maintaining the interferometric information during the upconversion. The laser beam provided by the narrow-band pump light source can for example have a spectral width which is lower than 10 nm, or 5 nm, or 1 nm, or 0.75 nm, or 0.5 nm, or 0.4 nm, or 0.3 nm, or 0.2 nm, or 0.1 nm.

In some embodiments, the wavelength of the pump light beam, $\lambda_P$, is in the range of 600 nm to 1.8 µm, such as in the range of 800 nm to 1.5 µm, such as in the range of 800 nm to 1100 nm.

It can be seen from the above equation that the wavelength of the upconverted photon always is smaller than the pump wavelength and the pump wavelength thus sets an upper limit to the wavelength range of the upconverted light beam. For example, a pump wavelength of below 1.5 µm provides that the wavelengths of the upconverted light beam are below 1.4 µm for interference light beam wavelengths up to 15 µm such that e.g. InGaAs or Ge-based spectrometers can be used to detect the upconverted light beam. Such spectrometers are both faster and can be acquired at a lower cost compared to detectors normally used for detecting light with a wavelength of several micrometers. Using a pump wavelength below 1100 nm, such as a pump wavelength of 1064 nm, provides that for an interference light beam with light at wavelengths in the range of 3 µm to 12 µm the wavelengths of the generated upconverted light beam are below 1000 nm and that low-cost conventional Si-CMOS detectors hence can be used for detecting the upconverted light beam.

Using a pump light source with a wavelength, $\lambda_P$, which is smaller than the wavelength, $\lambda_{IR}$, of the photons that are upconverted, provides that the sum frequency generated photons have a wavelength, $\lambda_{UP}$, which is less than half the wavelength of the interference light beam photon that is upconverted, i.e. $\lambda_{UP} < 0.5 \cdot \lambda_{IR}$ when $\lambda_P < \lambda_{IR}$.

Sum frequency generation in pumped nonlinear elements with the wavelength of the pump beam being similar to the wavelength of the upconverted light beam (often referred to as Second Harmonic Generation), can only offset the wavelength of the upconverted photon with a factor 2 and hence cannot upconvert light in an interference light beam at wavelengths over 2.8 µm into a wavelength range where low-cost and fast near-infrared and visible detectors are commercially available.

An advantage of using a short wavelength pump beam of the upconversion module for the frequency upconversion is hence that the wavelength range of the generated upconversion light beam (e.g. as defined by a wavelength range extending between $\lambda_3$ and $\lambda_4$) is offset by more than a factor of two towards shorter wavelengths relative to the wavelength range of the probe light beam (e.g. as defined by a wavelength range extending between $\lambda_1$ and $\lambda_2$).

In some embodiments, the upconversion element is arranged in a cavity. This may provide the advantage that the efficiency of the frequency upconversion is increased when the pump light beam or the interference light beam propagates through the upconversion element two or more times before leaving the upconversion module.

Nonlinear crystals or equally suitable nonlinear materials configured to provide upconversion by a parametric process, such as by sum frequency generation, may be used as nonlinear elements in the upconversion module. The quadratic nonlinear material may be a crystal such as a lithium niobate, lithium tantalite, potassium niobate, $LiGaS_2$, or AlGaAs/GaAs crystal which all have an effective non-linear coefficient, den, which is larger than 0.1 pm/V. Accordingly, in some embodiments, the nonlinear element comprises a nonlinear crystal with an effective non-linear coefficient, den, which is larger than 0.1 pm/V, such as larger than 0.5 pm/V, such as larger than 1 pm/V. Other suitable materials employed for upconversion could be: GaP, GaN, an element from the KTP family, ZGP, GaSe, CSP, BBO, LBO or KDP.

For a probe light beam with a spectrum in the range of 2.8 µm to 4.5 µm and having a bandwidth in the range of 300 nm to 2000 nm a Lithium Niobate crystal may be applied while for a probe light spectrum in the wavelength range of 3 µm to 8 µm a Lithium Gallium Sulphide crystal may be used in the upconversion. The crystals are only examples and other types may be used, such as a $AgGaS_2$ crystal, a GaP crystal or a ZGP crystal.

In some embodiments, the pump light beam provided by the pump source of the upconversion element may be pulsed. Using a pulsed pump beam may provide the advantage that the pump beam intensity, which drives the upconversion, can be increased during the relative short pulses compared to a constant lower intensity of an un-pulsed pump. Using a continuous wave (CW) laser beam for pumping the upconversion element can help to improve the spectral resolution of the OCT system and to increase an imaging depth of the signal obtained from a sample.

In some embodiments, the upconversion pump light beam is pulsed, synchronized and overlapping with the pulses of the interference light beam to improve the efficiency of the nonlinear interaction generating the upconverted light. The upconversion pump light beam can also be a CW laser beam.

The upconversion module may be configured to employ a pump light beam having a wavelength $\lambda_P$ which is smaller than the first wavelength $\lambda_1$ for frequency upconverting the light in the wavelength range between the first wavelength $\lambda_1$ and the second wavelength $\lambda_2$.

A configuration with $\lambda_P < \lambda_1$ provides the advantage that the generated upconverted light beam has wavelengths well below the wavelengths of the interference light beam and thus that mid-infrared probe light beam can be used to analyze the sample while a detector operating at wavelengths well below the mid-infrared range can be applied for the detection.

In some embodiments, the upconversion module at least partly operates by non-collinear interaction between the interference light beam and the pump light beam. When the conditions for non-collinear phase-matching of the signals are satisfied in the upconversion module, i.e. $k_{up} \approx k_P + k_{IR}$ the upconversion is highly efficient.

In some embodiments, the ratio between the bandwidth of the interference light beam and the bandwidth of the upconverted light beam is more than 2, such as more than 3, such as more than 4, such as more than 5, such as more than 6, such as more than 8, such as more than 10, such as more than 15, such as more than 20.

A large ratio between the bandwidth of the probe light beam and the bandwidth of the upconverted light beam may provide that the entire upconverted interference light beam can be detected by a single detector covering a relatively narrow wavelength range without a tuning of the sensor elements in the detector thereby providing fast and cost effective detection of the interference light beam.

Supercontinuum Source

In some embodiments, a broadband light source of the OCT system comprises a supercontinuum source. The supercontinuum source is preferably configured for providing a supercontinuum extending over at least part of the mid-infrared range. The supercontinuum may therefore comprise light within a wavelength range from 2.6 µm to 20 µm. The supercontinuum may also comprise light at wavelengths outside the mid-infrared range, such as e.g. a supercontinuum extending from 0.9 µm to 4.5 µm. Using a broadband light source based on a supercontinuum source can be advantageous since supercontinuum sources can provide light over a wide and continuous range of wavelengths, such as light with a large center wavelength and a bandwidth of several microns which—as explained—can be employed to simultaneously provide a good axial resolution and penetration depth in an OCT system.

In some embodiments, the supercontinuum source is based on a solid state laser, or a master-oscillator power amplifier (MOPA) or a fiber laser, such as 2.8 µm Er:ZBLAN lasers, or a 1.9 µm Tm:Silica fiber lasers pump, and a nonlinear fiber, where the supercontinuum is generated when pulses from the laser or the MOPA pump propagate through the nonlinear fiber to generate the supercontinuum. In some embodiments, the nonlinear fiber comprises a zirconium fluoride fiber (ZBLAN), a Tellurite fiber (TeO2), an indium fluoride fiber (InF3), an arsenic sulfide (e.g., $As_2S_3$) fiber, an arsenic selenide (e.g., $As_2Se_3$), Germanium arsenic selenide (Ge—As—Se) and/or a highly Germania ($GeO_2$) doped silica fiber, or combinations of these. The fibers may be single or multimode fibers. The fibers may be step-index fibers or photonic crystal fibers.

Long-Pass Filter

In some cases the broadband light source provides light over a wavelength range which is broader than required and/or desired for the OCT system and it may be advantageous to reduce the bandwidth of the light source, e.g., by using one or more filters. For example, a supercontinuum source based on a 1.55 µm master-oscillator power amplifier (MOPA) pump laser and a single-mode ZBLAN fiber can generate a continuous spectrum from 0.9 to 4.7 µm carrying a substantial amount of energy, which may cause unwanted heating of various components or the analyzed object. Accordingly, in some embodiments, the system comprises a filter, such as a long-pass filter, arranged to block wavelengths in the light from the broadband light source below a cut-on wavelength. The cut-on wavelength may define the first wavelength $\lambda_1$ of the probe light spectrum projected onto the analyzed object.

The filter may be part of the broadband light source and may be arranged before the probe light beam reaches the interferometer or be arranged in relation to the interferometer, or in the sample path of the interferometer before the probe light reaches the analyzed object. The light provided by the supercontinuum source may be filtered before being projected onto the object and the analyzed object may only be exposed to light in the range starting from a cut-on wavelength. This may be advantageous when the light source provides light over a very wide range of wavelengths while the upconversion module only is capable of upconverting light in a portion of this wavelength range. The sample is then protected from the full and often quite intense signal from the supercontinuum light source and the quality of the measurements is not degraded since this is determined by the bandwidth of the upconversion module. When the components of the interferometer are sensitive to highly intense signals it may be advantageous that the long-pass filter is part of the broadband light source or is arranged between the broadband light source and the interferometer to protect the fragile components in the interferometer from the full intensity of the supercontinuum.

For example in connection with the mentioned MOPA—ZBLAN supercontinuum source, a long pass filter blocking light below 3.5 µm may be applied to provide that the probe light beam launched onto the analyzed object has a spectrum with a center wavelength of 4 µm and a bandwidth of around 1000 nm. Filtering away the short wavelength portion of the supercontinuum spectrum provides the advantage that unnecessary heating of optical elements and/or the scanned object (e.g., a part of the human body) is avoided. Furthermore the truncating of the supercontinuum spectrum can make the task of handling the light beams in the interferometer, the upconversion and the detection of the upconverted light beam easier.

A filter used in the OCT system can be a bandpass filter. The filter can be configured to block out any wavelengths longer than what is supported by the upconversion module. Optionally, the filter can be configured to block out any wavelengths shorter than the shortest wavelength which is supported by the upconversion module.

Interferometer

The interferometer may have an input where the probe light from the broadband light source is received. A beam dividing element divides the received probe light into a sample path and a reference path where probe light propagating along the sample path can be directed towards the object to be analyzed. The probe light propagating along the reference path is reflected backwards along the reference path to the beam dividing element by a reflective element, such as a mirror, arranged in the reference path. Probe light backscattered from the analyzed object is collected and propagates backwards along the sample path to interfere with the probe light reflected from the reflective element in the reference path thereby generating an interference light beam. For a free-space interferometer, the beam dividing element may be a beam splitter arranged in the path of the incoming probe light delivered by the light source. For a fiber based interferometer, the beam dividing element may be a fiber based coupler.

Fiber-Based Interferometers

In some embodiments, the interferometer comprises a fiber based optical coupler that divides the received probe light into two optical fibers forming part of the sample and reference paths. Current state of the art broadband fiber based couplers are limited in bandwidth to about 300 nm. I.e. the coupling efficiency is substantially constant over a 300 nm wavelength range. The interferometer thus sets the limitation on the effective bandwidth of the OCT system and increasing the bandwidth of the probe light will not be expected to increase the axial resolution of the measurements provided by the OCT system (assuming that the probe light spectrum and the sensor elements are aligned with respect to wavelength). For some applications it can still be advantageous to employ a fiber based coupler since this allows for an all-fiber system which can provide a stable setup with a flexible sample arm that guides the probe light to the analyzed object and collects the reflected probe light.

Free-Space Interferometers

The beam dividing element and other optical elements of a free-space interferometer can often operate over a wavelength range which is significantly broader than 300 nm. The bandwidth of free-space interferometers can easily be above 600 nm such as above 1000 nm. Typically, optical elements such as lenses or mirrors, e.g. parabolic mirrors, are arranged to receive the probe light from the broadband light source and guide the probe light towards the beam dividing element. From the beam dividing element one portion of the probe light propagates along the free-space reference path to the reference element and another portion propagates along the free-space sample path to the analyzed object. The beam dividing element can be a beam splitter.

Any type of interferometer may be used, such as a Michelson Interferometer or a lateral shearing-/Fabry Perot-/Fizeau interferometer for which the interferometer can be made very compact as few optical components are needed. The interferometer may also be a Mach-Zender interferometer which allows easy access and manipulation of the incoming and outgoing beams relative to the sample and reference reflectors. Any combination of one of more interferometers makes it possible to combine several OCT systems (multi-model OCT) operating with different central probe beam wavelengths.

Optical System

In addition to the interferometer, the OCT system may comprise further optical elements such as reflectors, lenses and optical waveguides for delivering the probe light from the source to the analyzed object and for receiving the probe light reflected from the analyzed object and guiding it to the detector, and/or further optical components for shaping or altering the properties of the different light beams propagating in the system.

In some embodiments, the system comprises at least one reflector, such as a parabolic mirror, arranged in the sample path for directing the probe light beam along the sample path towards the analyzed object and for collecting probe light back-scattered from the analyzed object. Using a reflector may provide the advantage that chromatic aberrations are avoided. In lenses such aberrations may be pronounced for a broadband probe light and OCT systems where the sample arm utilizes lenses for collimating and interfacing the probe beam may suffer from chromatic aberration related problems.

The probe beam may be scanned across the analyzed object by translating (at least the sample arm of) the optical system and the analyzed object relative to each other. E.g. by translating the optical system and/or sample arm and/or the analyzed object using one or more translation stages.

Detector

In some embodiments, the detector is configured for detecting light within a range of wavelengths extending from 390 nm to 2 µm, such as in the range of 390 nm to 900 nm or in the range of 900 nm to 1600 nm. Detectors operating in the near-infrared and/or visible wavelength range can be used to extract the interferometric information provided by the interference light beam once the upconversion module has generated a light beam at the near-infrared or visible wavelengths containing the same interferometric information as the mid-infrared interference light beam. The wavelength range of the detector may extend outside the visible and near-infrared range, such as InGaAs detectors operating for example in the range of 900 nm to 1600 nm or in the range of 700 to 2600 nm.

In some embodiments, the detector comprises a spectrometer, such as a silicon-based, Ge-based or InGaAs-based spectrometer.

One advantage of using such spectrometer is that fast detection over the entire relevant wavelength range can be achieved and such spectrometers can be compact and provide a good spectral resolution at a relatively low cost compared to detectors for the mid-infrared range. For spectrometer based OCT to be fast and provide a good resolution, the spectrometer is preferably capable of recording spectra of the interference light beam with several thousands of detector elements, such as pixels, in short time. This can be provided by visible and near-infrared spectrometers.

The upconversion module and the detector may be parts of a broadband detector, such as integrated parts of the broadband detector.

At least some embodiments of an OCT system in accordance with the present invention may be advantageous as they may not only allow a detection of a mid-IR interferometric signal, but a detection of the signal without sacrificing the detection speed, sensitivity, and resolution of the system. A spatially and temporally incoherent light source might for example be efficiently coupled to an optical fiber. A broadband light source (having a spectral width of more than 300 nm) might be employed to obtain an interference light beam from a sample, followed by an instantaneous parallelized upconversion of the entire spectrum (as opposed to slow scanning). A sufficiently narrow linewidth of the pump laser (for example smaller than 0.5 nm), and an efficient fiber coupling to and from the upconversion module might help to obtain a large imaging depth and a high spectral resolution when analyzing an up-converted signal in a spectrum analyzer or a spectrometer or a spectrograph.

A fiber used for fiber coupling can for example act as a beam filter and ensure 100% beam overlap for detection, plus it can govern the achievable spectral resolution. A small fiber core diameter can lead to a high resolution, and a large fiber core diameter can lead to a low resolution.

In addition, detecting the interferometric signal of at least 300 nm can require a nontrivial design of the upconversion system in order to have a sufficient signal-to-noise ratio across the entire bandwidth as well as an equal up-conversion efficiency to ensure a spectral shape suited for OCT. A heavily warped spectrum may distort the OCT image beyond recognition.

Beams having a concentric spatial light pattern can originate from the upconversion module. A challenge in coupling concentric spatial light patterns to a single mode optical fiber guiding light to a conventional spectrometer requires efficient power coupling to reach a signal level necessary for OCT utility (speed/real-time imaging/>100 lines per second) and a mode transformation from the concentric pattern and to one approaching the mode of the spectrometer delivery fiber (fundamental single Bessel-like mode of the delivery optical fiber) to provide a spectral resolution necessary for an applicable OCT imaging range.

BRIEF DESCRIPTION OF THE DRAWINGS

The above and/or additional objects, features and advantages of the present disclosure, will be further elucidated by the following illustrative and exemplary detailed description of exemplary embodiments of the present disclosure, with reference to the appended drawings, wherein.

DETAILED DESCRIPTION

Figure 1:
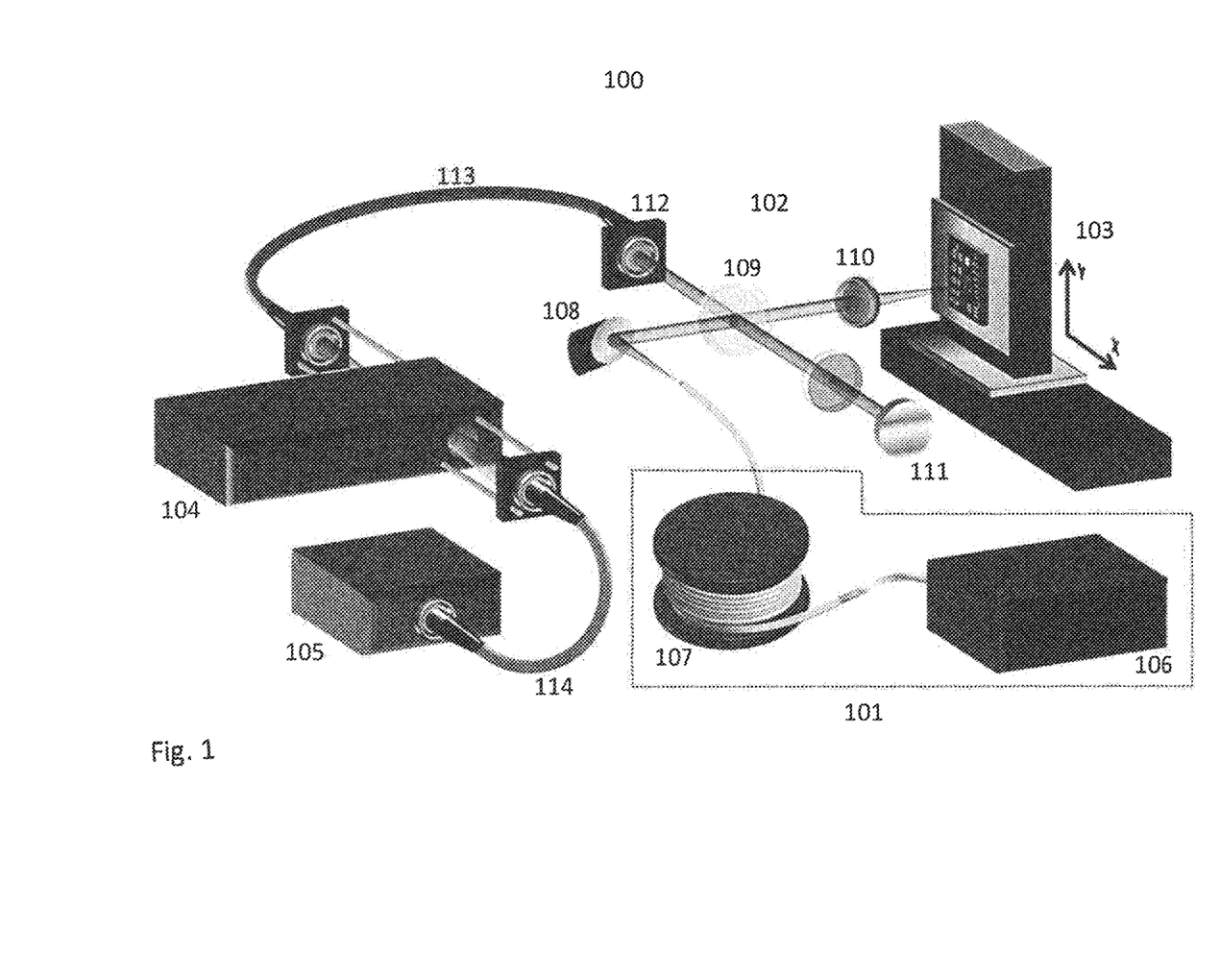
FIG. 1 shows an OCT system.

FIG. 1 shows an overview of an embodiment of the OCT system operating with probe light having a center wavelength of 4 µm and using a NIR/VIS detector. The illustrated OCT system 100 has five modular parts: a broadband light source 101, a Michelson interferometer 102, a scanning sample translation system 103, a frequency upconversion module 104, and a silicon CMOS-based spectrometer 105. Each optical subsystem is connected via optical fiber to ease the coupling and alignment between subsystems. This is only an option. Also free-space connections between subsystems are possible.

The broadband light source 101 has a supercontinuum source based on a 1.55 µm master-oscillator power amplifier (MOPA) 106 pump laser and a zirconium fluoride fiber 107. Optionally, the fiber 107 may be a single-mode fiber, for example in the 3.5-4.5 µm region. The MOPA is for example a four-stage MOPA using an unfolded double-pass amplifier configuration based on a 1.55 µm directly modulated seed laser diode. The seed pulse duration is for example 1 ns, and the repetition rate is for example tunable between 10 kHz and 10 MHz. The seed is for example subjected to three stages of amplification in erbium-doped and erbium-ytterbium-doped silica fibers, which extend the spectrum to 2.2 µm by in-amplifier nonlinear broadening. Preferably, in order to further push the spectrum towards longer wavelengths, the erbium fiber is spliced to approximately 40 cm of 10 µm core diameter thulium-doped double-clad fiber which extends the supercontinuum spectrum to 2.7 µm. Further preferably, the thulium-doped fiber is subsequently spliced to a short piece of silica mode-field adapter fiber having a mode-field diameter of 8 µm, which provides a better match to the fluoride fiber 107. The mode adapter fiber is butt-coupled to a 6.5 µm core diameter single-mode ZrF4-BaF2-LaF3-AlF3-NaF (ZBLAN) fiber with a short length of around 1.5 m to reduce the effect of strong multi-phonon absorption beyond 4.3 µm.

The supercontinuum source 101 for example produces a continuous spectrum from 0.9-4.7 µm and is for example set to operate at 1 MHz pulse repetition rate generating 40 mW of average power above 3.5 µm. The spectral components below 3.5 µm may be blocked by a long-pass filter of the broadband light source (not illustrated in the figure for reason of simplicity), such that the probe light provided to the interferometer is a broadband spectrum with for example a bandwidth of 1.2 µm and a center wavelength at 4 µm with an average power of 20 mW being coupled to the sample arm of the interferometer.

The interferometer 102 is based on a Michelson design employing as an example a gold coated parabolic mirror collimator 108, a broadband $CaF_2$ wedged plate beam splitter 109, a $BaF_2$ plano-convex lens 110 in the sample arm, and a $BaF_2$ window and flat silver mirror 111 in the reference arm. The $BaF_2$ lens 110 may be chosen to minimize the effect of dispersion, while having a relatively short focal length of 15 mm. At 4 µm the dispersion of $BaF_2$ is relatively low at 16.4 ps $nm^{-1}$ $km^{-1}$ compared to other standard lens substrates, such as $CaF_2$ (33.0), Si (−45.8), and ZnSe (−59.9), but most importantly the dispersion slope is flat from 3.5-4.5 µm (13.6-19.1 ps $nm^-km^{-1}$). Even so, the residual dispersion from the 6.3 mm center thickness lens is roughly compensated by a 5 mm window and the remaining dispersion is compensated numerically. Coupling to the upconversion module 104 is performed using for example a 6 mm focal length aspheric chalcogenide lens 112 and for example a 9 µm core diameter single-mode indium fluoride patch cable 113.

Optics

The probe light beam in the sample arm of the interferometer is focused onto the analyzed object using for example a barium fluoride ($BaF_2$) lens 110, and 2D and 3D images are acquired by moving the sample using a sample translation system 103 having motorized translation stages for moving the analyzed object in a plane perpendicular to the incoming probe light. The interfering sample and reference signals are then collected in the indium fluoride fiber 113, which may be for example a single-mode fiber, and the generated interference light beam relayed to the upconversion module 104 for frequency upconversion to the near-IR wavelength range. The upconverted light beam is then coupled to a silica fiber 114 and imaged onto the spectrometer 105 to resolve the spectrum. The silica fiber 114 is preferably a single-mode, or alternatively a multi-mode fiber.

Upconversion

The illustrated OCT system 100 operates with a center wavelength of 4 µm with more than 1 µm spectral bandwidth. Accordingly, the upconversion module is designed and optimized to upconvert the entire spectral range from 3.6-4.6 µm for fastest detection. Quasi-phase matching in a periodically poled lithium niobate (PPLN) crystal is used for the broadband upconversion, owing to its design flexibility, access to a high $d_{eff}$ (14 pm/V), and optical transparency up to 5 µm.

The upconversion takes place inside the PPLN crystal, where each wavelength is phase-matched at a different propagation angle. Thus non-collinear interaction among the three participating light beams is considered to phase-match over a wide spectral range. As the wavelengths of the upconverted light beam are below the pump wavelength, by choosing the pump wavelength at 1 µm, a spectrometer 105 employing conventional Si-CMOS detection can be employed for the detection of the upconverted light beam. Here, a solid state ($Nd:YVO_4$) continuous wave (CW) linearly polarized laser operating at 1064 nm is used as the pump source. This pump source is for example driven by a broad area emitting laser diode (3 W, 880 nm). A high finesse folded solid state laser cavity may be formed by mirrors that all are HR-coated for 1064 nm and AR-coated for 700-900 nm. One mirror may act as output coupler for the upconverted light beam while other mirrors may be placed in a separate compartment to filter out the fluorescence from the laser crystal and the 1064 nm pump laser. The PPLN crystal is preferably a 20 mm long, 5% MgO-doped PPLN crystal (Covesion, preferably AR coated for 1064 nm, for example 2.8-5.0 µm on both facets). The PPLN crystal may consist of five different poling periods (Λ) ranging from 21-23 µm in steps of 0.5 µm. Each poled grating may have a 1 mm×1 mm aperture and may be separated by 0.2 mm wide regions of un-poled material. For different values of Λ, the phase-mismatch and hence the overall upconversion spectral bandwidth varies. Wider bandwidth requires larger input angles for the mid-infrared beam, which reduces the overall Quantum Efficiency (QE) as the effective interaction length is reduced. A CW intracavity power of >30 W at 1064 nm may be realized with a spot size (beam radius) of 180 µm inside the PPLN crystal. The mid-IR light (output of the fiber coupled 4 µm OCT signal), i.e. the interference light beam, is collimated and then focused into the PPLN crystal using for example a pair of CaF2 aspheric lenses (f=50 mm, AR coated for 2-5 µm). The upconverted light is collimated for example by a silica lens (f=75 mm, AR coated for 650-1050 nm). A short-pass (SP) 1000 nm and a long-pass (LP) 800 nm filter is for example inserted to block the leaked 1064 nm beam and 532 nm parasitic second harmonic light, respectively. The upconversion module may be able to upconvert all wavelengths in a relatively broad spectral range of 3.6-4.8 µm to a wavelength range of 820-870 nm, where fast and cost-efficient detectors can capture the spectral distribution of the upconverted light beam. The upconversion module may provide a fast generation of the upconverted light beam from the interference light beam to a shorter wavelength. The entire system is operated at room temperature.

Detection, Scanning and Data Processing

After the upconversion module 104 the near-IR light may be collected by a 50 µm core multimode silica fiber 114 guiding the light to a line scan spectrometer 105 (Cobra UDC, Wasatch Photonics, USA) operating for example with a maximum line rate of 45 kHz (for a bit depth of 10). The spectral range may cover wavelengths of 796 nm to 879 nm, which is for example sampled by 4096 pixels. To scan the sample, this is mounted on a double translation stage 103 (e.g., 2×ILS50CC from Newport) with for example a maximum travel speed of 100 mm/s, a travel range of 50 mm and a stepping resolution of 1 µm. The detected raw spectra are dark signal subtracted and normalized to the reference arm signal. Pixel to wavenumber translation and interferometer dispersion compensation is achieved by exploiting phase information across the pixel array retrieved for two reference interferograms showing clear interference fringes. In this way spectral resampling is performed to linearize wavenumber sampling after which a phase shift is applied for compensating the unevenly matched dispersion in the arms of the interferometer. To suppress effects stemming from the spectral envelope of the interferograms, a Hanning spectral filter is applied to the spectral region of the interferometric signals. Finally a fast Fourier transform (FFT) is applied to generate a reflectivity profile, a so-called A-scan. A compromise between signal strength and acquisition time is made that leads to an A-scan acquisition time of 3 ms. To build B-scans (2D images), the horizontal stage (X) is programmed to move continuously over a specified distance, achieving a 500 line B-scan in 1.5 seconds. 3D scans are built by stepping the vertical (Y) stage at a proportionate slower rate to assemble multiple B-scans.

As mentioned above, the sample can be scanned by mounting the sample on translation stage 103. The scanning can also be carried out by moving one or more optical elements, such as mirrors, in such a way that the light scans over the sample. In particular, a galvanometric scanning device could be employed. The galvanic scanning device could be coupled to one or two or more scanning mirrors and the device could control the one, two or more mirrors to move the light beam over the sample surface. Galvanic scanning could be fast and might help to remove artefacts from the image of the sample.

Figure 2:
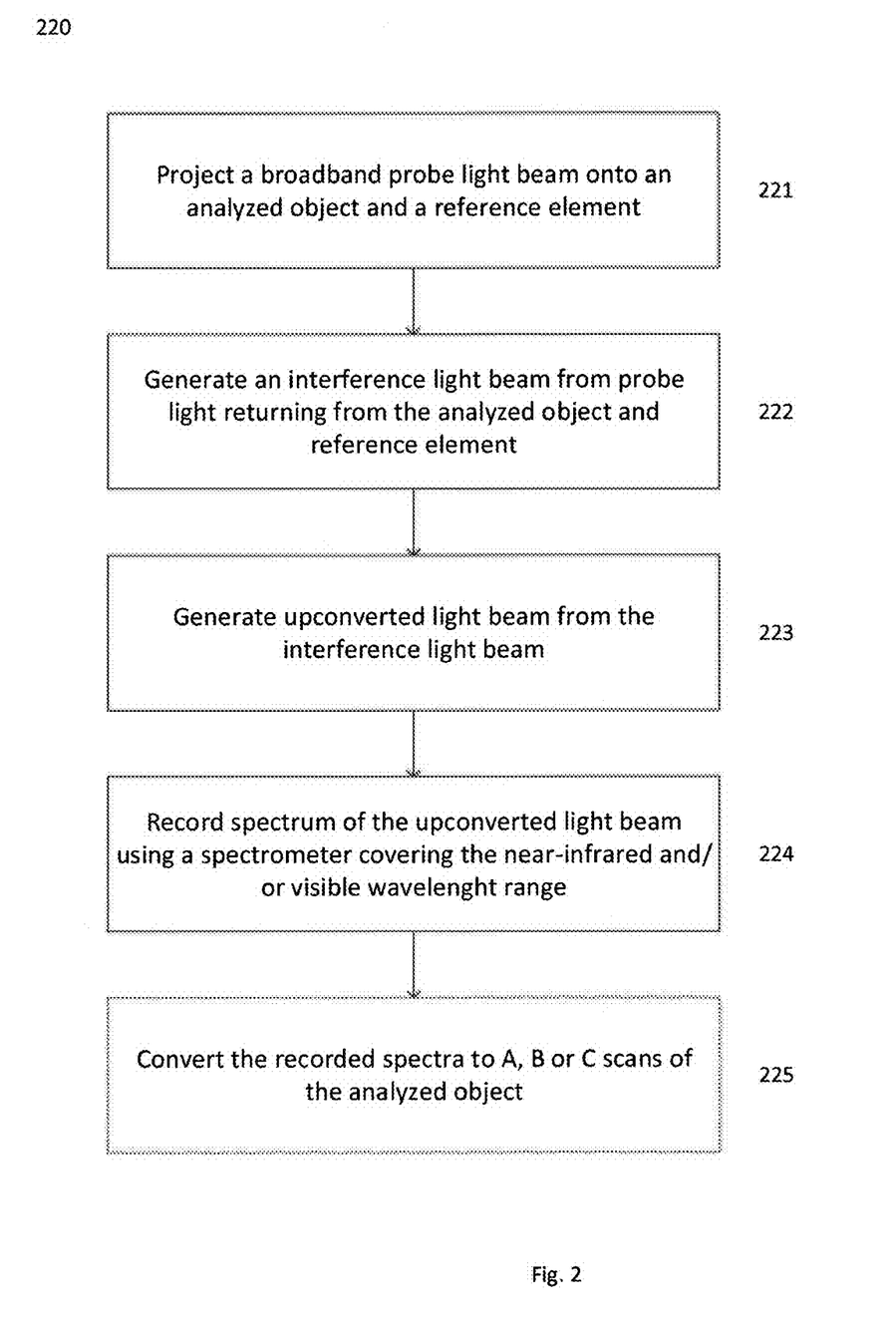
FIG. 2 shows a flowchart for a method.

FIG. 2 shows a flowchart 220 of a method for recording OCT data, such as for determining an A scan of an analyzed object.

In step 221, the broadband probe light beam is projected onto the analyzed object and a reference element. The probe light beam is generated by passing light from a supercontinuum source as the one described above in relation to FIG. 1 through a long-pass filter. In the example of FIG. 1, the supercontinuum source provides light over a wavelength range from 0.9 µm to 4.7 µm which is wider than the bandwidth of the upconversion system that extends for example from 3.5 µm to 4.7 µm. To avoid heating of, e.g., optical components by wavelengths outside the bandwidth of the upconversion system, the supercontinuum is sent though a long-pass filter narrowing the bandwidth of the probe light to 3.5-4.7 µm. The probe light is launched from the broadband light source into an interferometer where a beam splitter divides the probe light into sample path and a reference path. The analyzed object is placed in the sample path such that the corresponding portion of the probe light is projected onto the object. The remaining portion propagates to the reference element which is located in the reference path and is reflected therefrom to interfere with probe light backscattered from the analyzed object to generate an interference light beam (step 222). The generated interference light beam covers substantially the same wavelength range as the truncated probe light spectrum (i.e. after the long-pass filter), such that the interference light beam primarily is at mid-IR wavelengths.

Detectors operating in the mid-IR range are significantly more expensive and much slower than detectors operating in the near-IR or visible wavelength range. In order to enable detection of the interference light beam using such low-cost and fast visible/near-IR detectors, the interference light beam is frequency upconverted from the wavelength range of the probe light to the near-IR and/or visible wavelength range in step 223.

The upconversion is performed by launching the interference light beam into a nonlinear crystal which is simultaneously pumped by an upconversion pump beam. The pump beam has a narrow linewidth, preferably single-frequency, to ensure that the upconversion does not cause a blurring of the spectral characteristics of the interference light beam. The pump beam and the interference beam interact through sum frequency generation such that photons of the upconversion light beam having a wavelength $\lambda_{UP}$ according to:

$$\lambda_P^{-1} + \lambda_{IR}^{-1} = \lambda_{UP}^{-1}$$

are generated, where $\lambda_{UP}$ is the pump wavelength and $\lambda_{IR}$ is the wavelength of a photon of the received interference light beam. The upconversion generates a compressed version of the spectrum of the interference light beam having similar spectral structures as the interference light beam and containing the same interferometric information, with the generated upconverted light beam at wavelengths below the pump wavelength. Low-cost powerful pump sources emitting light at a pump wavelength of 1064 nm are available. Using such a pump source provides that the spectral distribution of the generated upconverted light beam is at wavelengths where fast and low-cost near-infrared/visible detectors operate.

In step 224, the spectrum of the upconverted light beam is recorded using a detector operating in the near-IR and/or visible wavelength range. An upconverted light beam spectrum can be recorded for each position of the probe light beam on the analyzed object.

A so-called A-scan of the object can be determined by analysis of the recorded spectrum (optional step 225). The A-scan expresses the variations in the refractive index of the object from the surface and below, with a penetration depth determined from wavelengths of the mid-IR probe light into the object and an axial resolution which is improved by the large bandwidth if the probe light.

Figure 3A:
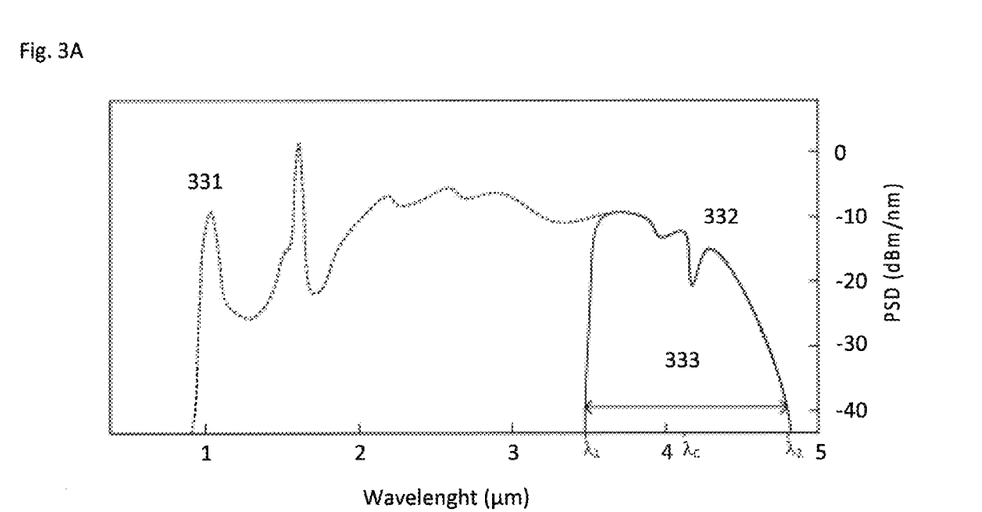
FIG. 3 shows examples of spectra.

FIG. 3 shows examples of spectra. In FIG. 3A, the dotted line 331 shows the 0.9-4.7 µm supercontinuum generated by the MOPA pump laser and zirconium fluoride fiber described above in relation to FIG. 1 while the solid line 332 shows the truncated probe light spectrum extending between 3.5 µm and 4.7 µm defined by using a long-pass filter to block the part of the supercontinuum light below 3.5 µm. The probe light provided to the interferometer and projected onto the analyzed sample is hence the truncated supercontinuum having a bandwidth 333 of 1.2 µm, with wavelengths between $\lambda_1$ and $\lambda_2$, and with a center wavelength, $\lambda_C$, around 4.1 µm.

From the interferometer at least a portion of this probe light is projected onto the analyzed object and probe light backscattered from the object is captured and allowed to interfere with light from the reference arm, as also illustrated in FIG. 1.

Figure 3B:
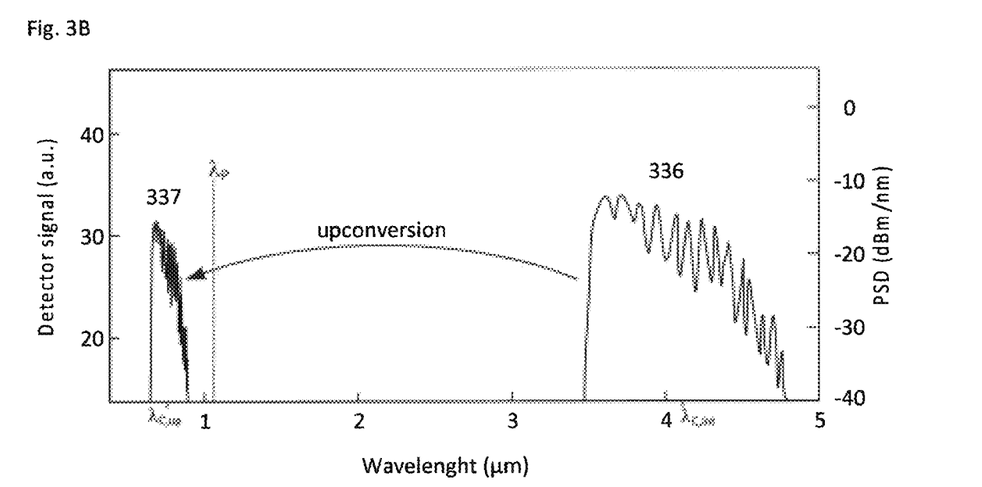

The resulting interference light beam has a spectrum 336 with a center wavelength $\lambda_{C,int}$ illustrated in FIG. 3B and carries interferometric information expressing the refractive indices of sub-surface structures of the analyzed object. The center wavelength being the average value between $\lambda_1$ and $\lambda_2$.

The upconversion module is configured to frequency upconvert light in the wavelength range between $\lambda_1$ and $\lambda_2$. Thus, the truncated supercontinuum is filtered out in such a way that at least in substance all wavelengths in the truncated supercontinuum can be upconverted by the upconversion module. The truncated supercontinuum may also be spectrally broader, but only the wavelengths between $\lambda_1$ and $\lambda_2$ are subject for upconversion by the upconversion module.

The upconversion of the interference light beam is driven by the pump beam of the upconversion module with a wavelength $X_p$=1064 nm (indicated by the dotted line in FIG. 3B) and shifts the spectrum to wavelengths below $\lambda_p$ and simultaneously compresses the interference beam spectrum such that a single detector unit operating in the visible/near-infrared region can be used for deriving the interferometric information from the upconverted light beam spectrum 337. In the illustrated example the wavelength of the pump light beam $\lambda_p$ is below $\lambda_1$ by a factor of more than 3, thus causing a large shift in the wavelengths of the generated upconverted beam compared to the wavelengths of the interference light beam.

Figure 4:
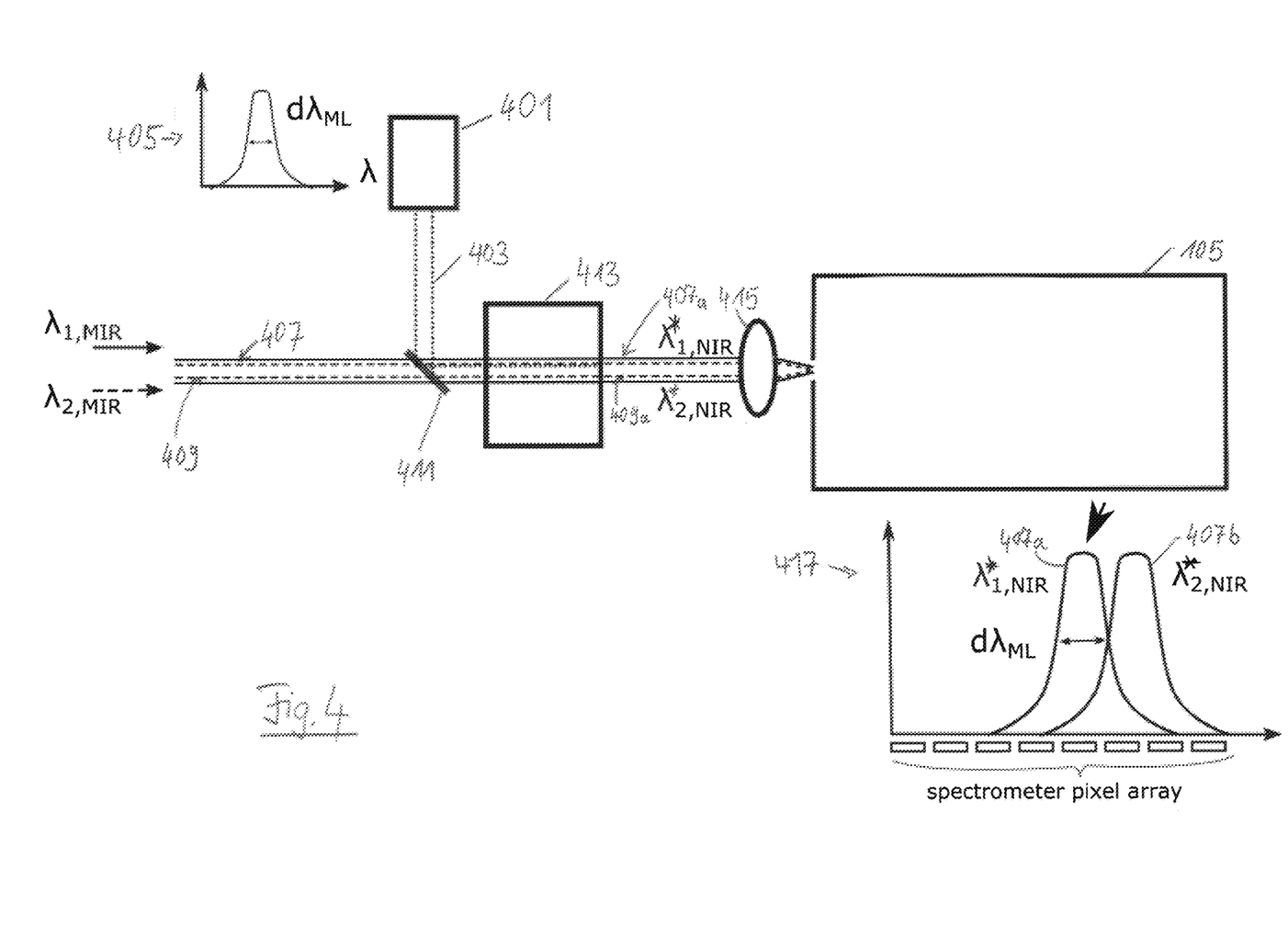
FIG. 4 shows schematically an example of an optical setup for upconversion.
Figure 5:
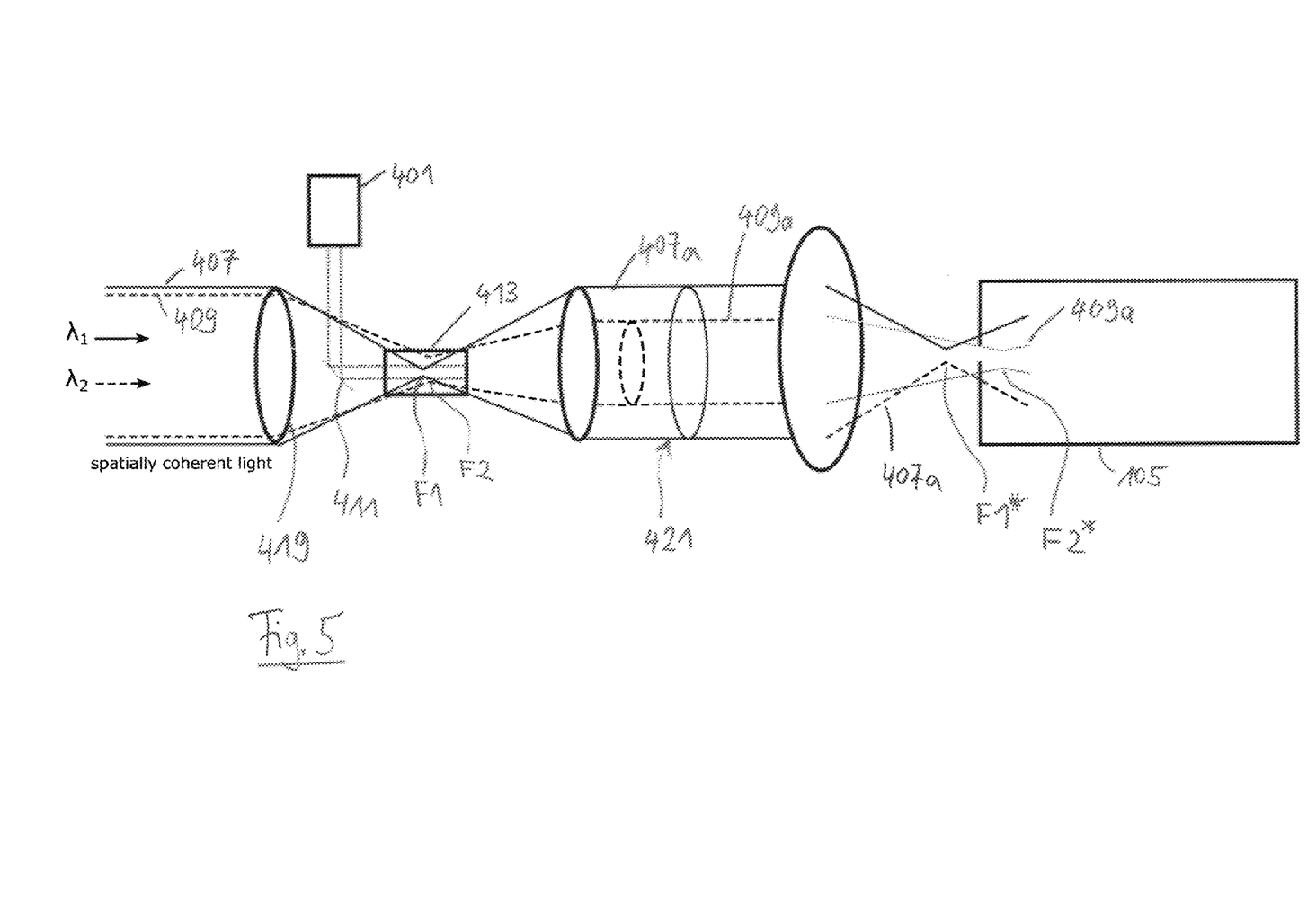
FIG. 5 shows schematically a further example of an optical setup for upconversion.

The optical setup as illustrated in FIG. 4 or FIG. 5 may be employed in an OCT system 100 as shown in FIG. 1.

Now referring to FIG. 4, a pump laser 401 is used as a pump source and provides a continuously operating pump light beam 403 that has a spectral width $d\lambda_{ML}$ as illustrated in graph 405 which shows the signal strength of the pump light beam 403 as a function of wavelength. The spectral width $d\lambda_{ML}$ corresponds to the full-width half maximum (FWHM) value of the signal shown in graph 405. The pump laser 401 can for example be a Nd:YAG laser providing a pump beam with a wavelength at 1064 nm.

The pump light beam 403 is reflected from mirror 411 which is transparent for an interference light beam 407 or 409 so that the pump light beam 403 and the interference light beam 407 or 409 travel collinearly through a nonlinear medium 413 used for upconversion in upconversion module 104. The pump light beam 403 and the interference light beam 407 or 409 travel through the nonlinear medium 413 in a non-focused fashion. More specifically, the pump light beam 403 and the interference light beam 407 or 409 travel collinearly through the nonlinear medium 413 as collimated beams.

In the nonlinear medium 403, a parametric process, such as a sum-frequency generation process, can cause the generation of an up-converted light beam 407a, 409a from the respective light beam 407, 409.

A focusing lens 415 is arranged to focus the up-converted light beam 407a, 409a into an entrance of spectrometer 105. The entrance can be formed by a free space entrance window, such as a pinhole, or by a fiber front face.

A graph 417 shows signal strengths as a function of wavelength as detected by the spectrograph 105 for the up-converted light beam 407a and the up-converted light beam 409a. As an example, the light beam 407 might include a wavelength Al in the mid-infrared region. The light beam 409 might include a wavelength $\lambda_2$ in the mid-infrared region (MIR). This wavelengths are up-converted to respective wavelengths $\lambda_1^*$ and $\lambda_2^*$ in the near-infrared region (NIR) and present in the respective beams 407a, 409a.

As shown in the graph 417, the two up-converted wavelengths $\lambda_1^*$ and $\lambda_2^*$ can be spectrally resolved from each other if the distance between $\lambda_1^*$ and $\lambda_2^*$ is larger than the spectral width $d\lambda_{ML}$ of the pump light beam 403. It is therefore advantageous to employ a cw-laser beam as pump light beam having a very small spectral width $d\lambda_{ML}$, for example a spectral width $d\lambda_{ML}$ which is smaller than 0.5 nm.

The optical setup as shown in FIG. 5 differs from the setup of FIG. 4 in that the respective interference light beam 407, 409 is focused by use of focusing lens 419 in the nonlinear medium 413. The wavelength $\lambda_1$ in the beam 407 may therefore be focused to focal point F1, whereas the wavelength $\lambda_2$ in the beam 409 may be focused to focal point F2 which is different from F1.

An optical system 421 is employed to focus the respective up-converted light beam 407a, 409a into the entrance of spectrometer 105. Due to the different wavelengths $\lambda_1^*$ and $\lambda_2$ in the up-converted light beams, light beam 407a is focused to focal point F1* and light beam 409a is focused to focal point F2* which is different from F1*.

In view of the above, the setup of FIG. 4 is advantageous over the setup of FIG. 5, since in the setup of FIG. 4, focusing takes only place for coupling into the spectrometer, but the interference light beam is not focused in the nonlinear medium 413. Thus, the setup of FIG. 4 is better suited for resolving interference signals that include a larger range of frequencies.

Figure 6:
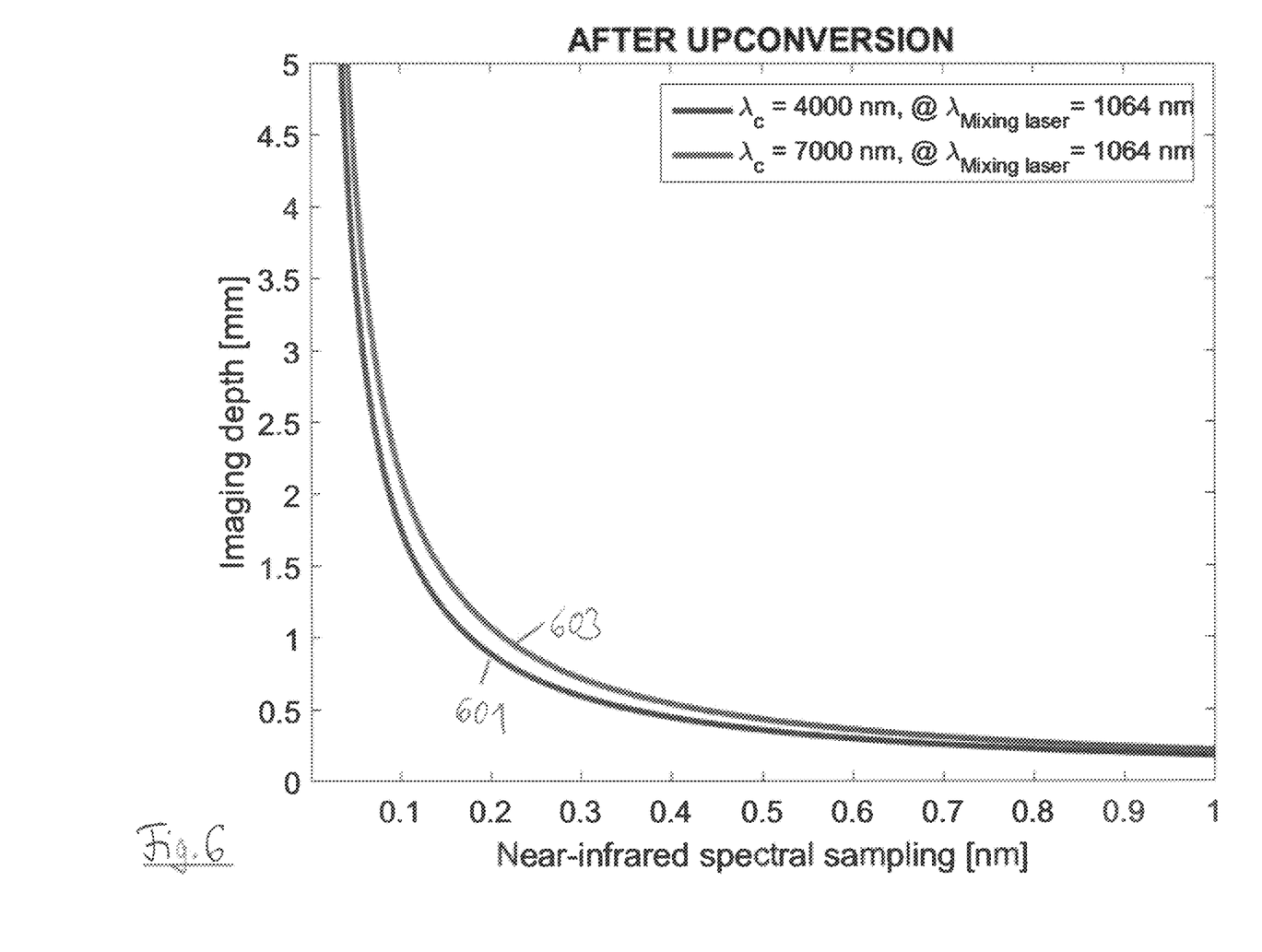
FIG. 6 shows a graph showing imaging depth as a function of spectral sampling.

FIG. 6 shows two signals 601 and 603 related to the imaging depth in millimeters as a function of the near-infrared spectral sampling in nanometers. The signal 601 is obtained from light at a center wavelength of 4000 nm and mixed with a pump beam at a wavelength of 1064 nm. The signal 603 is obtained from light at a center wavelength of 7000 nm and mixed with a pump beam at a wavelength of 1064 nm.

The near infrared spectral sampling corresponds to the line width (spectral width) of the pump signal. As shown, the imaging depth increases with decreasing line width. Preferably, a cw-pump beam having a line width of less than 0.5 nm is employed in order to obtain a high imaging depth.

LIST OF SELECTED REFERENCE NUMBERS 100 system
101 supercontinuum source
102 interferometer
103 translation system
104 upconversion module
105 spectrometer
106 master-oscillator power amplifier
107 zirconium fluoride fiber
108 mirror collimator
109 beam splitter
110 lens focusing probe beam onto object
111 reflective element
112 lens collecting light for upconversion
113 patch cable
114 multi-mode fiber
401 pump laser
403 pump light beam
405 graph
407 light beam
407a up-converted light beam 409 light beam
409a up-converted light beam
411 mirror
413 nonlinear medium
415 lens
417 graph
419 lens
421 optical system
601 signal
603 signal
F1, F1* focal point
F2, F2* focal point

What is claimed is:

1. An Optical Coherence Tomography (OCT) system, comprising:
an upconversion module configured to frequency upconvert light received or receivable by the upconversion module and which is in a wavelength range between a first wavelength and a higher second wavelength,
a light source, configured for providing a probe light beam, which has a spectrum that at least comprises a continuous spectral region between the first wavelength and the second wavelength, and
a detector configured to receive the frequency upconverted light from the upconversion module and for detecting spectral properties of the upconverted light,
wherein the difference between the second wavelength and the first wavelength is at least 300 nm or larger,
the wavelength range comprises a center wavelength at 2.8 μm or larger, and the center wavelength is defined by the average value between the first wavelength and the second wavelength,
wherein the upconversion module is configured to employ a pump light beam, having a wavelength which is smaller than the first wavelength, for frequency upconverting the light in the wavelength range between the first wavelength and the second wavelength,
wherein the pump light beam is continuous, and
wherein the pump light beam has a spectral width of not more than 1 nm.

2. The system in accordance with claim 1, wherein the wavelength range between the first wavelength and the second wavelength that can be frequency upconverted is a continuous wavelength range.

3. The system in accordance with claim 1,
wherein, the wavelength of the pump light beam, $\lambda_p$, is in the range of 600 nm to 1.8 μm, and/or
wherein the upconversion module at least partly operates by sum frequency generation using the pump light beam and light in the wavelength range, and/or
wherein the upconversion module does not employ second harmonic generation (SHG) for upconverting the light.

4. The system in accordance with claim 1, wherein the difference between the first wavelength and the second wavelength is smaller than 20 μm or 15 μm or 10 μm or 5 μm or 2 μm or 1 μm.

5. The system in accordance with claim 1, further comprising an interferometer configured for receiving a probe light beam from a light source and for dividing the received probe light beam into a sample path and a reference path and for generating an interference light beam by combining probe light returning from the sample path with probe light returning from the reference path,
wherein the upconversion module is configured to receive the interference light beam for generating an upconverted light beam by frequency upconversion of the interference light beam.

6. The system in accordance with claim 1, wherein the upconversion module comprises:
an upconversion element configured to enable parametric wavelength conversion, where the upconversion element comprises a quadratic nonlinear material; and/or
a pump source arranged for launching a pump light beam into the upconversion element.

7. The system in accordance with any claim 3,
wherein the upconversion module is adapted to employ a part of the probe light or of the interference light as a pump light beam in the pump upconversion module, and
wherein, the continuous wave pump light beam has a spectral width of not more than 0.5 nm.

8. The system in accordance with claim 1,
wherein the probe light beam is pulsed or continuous, and
wherein, when the probe light beam is pulsed, pulses of a pump light beam used in the upconversion module are synchronized with pulses of the probe light beam.

9. The system in accordance with claim 1, wherein the upconversion module at least partly operates by collinear or non-collinear interaction between the interference light beam and a pump light beam.

10. The system in accordance with claim 1,
wherein the probe light beam and/or the pump light beam is focused within an upconversion element of the upconversion module, or
wherein the probe light beam and/or the pump light beam is not focused or unfocused or non-focused within the upconversion element,
wherein, the probe light beam and/or the pump light beam travels as a collimated beam through the upconversion element.

11. The system in accordance with claim 1, wherein the detector is configured to detect light within a range of wavelengths extending from 390 nm to 2 μm.

12. The system in accordance with claim 1, wherein the detector comprises a spectrometer.

13. The system in accordance with claim 1, further comprising a long-pass filter arranged to block wavelengths in the light received from a broadband light source of the system below a defined cut-on wavelength.

14. A method for analyzing an object using an OCT system in accordance with claim 1,
the method comprising:
providing a probe light beam, which is a mid-IR probe light beam,
dividing the probe light beam into a sample path and a reference path, where the probe light in the sample path is projected onto the object;
generating an interference light beam by combining probe light returning from the sample path with probe light returning from the reference path;
generating an upconverted light beam by frequency upconversion of the spectral components in the interference light beam which are in a wavelength range between a first wavelength and a higher second wavelength, the difference between the second wavelength and the first wavelength being at least 300 nm or larger, wherein the wavelength range have a center wavelength at 2.8 μm or larger, the center wavelength is defined by the average value between the first wavelength and the second wavelength, and detecting the spectral properties of the upconverted light beam.

15. The system in accordance with claim 1, wherein the system is a mid-infrared (mid-IR) OCT system and the light source is a mid-IR broadband light source.

16. The system in accordance with claim 3, wherein the wavelength of the pump light beam, $\lambda_p$, is in the range of 800 nm to 1.5 µm.

17. The system in accordance with claim 11, wherein the detector is configured to detect light within a range of wavelengths selected from the group consisting of the range of 390 nm to 900 nm and the range of 900 nm to 1600 nm.

18. The system in accordance with claim 12, wherein the spectrometer is a silicon-based, Ge-based or InGaAs-based spectrometer.

* * * * *